United States Patent [19]
Sylvester et al.

[11] Patent Number: 5,837,288
[45] Date of Patent: Nov. 17, 1998

[54] METHODS FOR STORAGE OF SEQUENCING GELS AND STORED SEQUENCING GELS USED BY SUCH METHODS

[75] Inventors: Keith Vincent Sylvester, San Diego; Joseph Sorge, Rancho Santa Fe, both of Calif.

[73] Assignee: Stratagene, La Jolla, Calif.

[21] Appl. No.: 587,879

[22] Filed: Jan. 11, 1996

[51] Int. Cl.⁶ .............................. C25B 1/00; C25B 7/00; B01D 61/42
[52] U.S. Cl. .................. 424/484; 204/182.1; 204/182.8; 204/299 R; 204/301
[58] Field of Search ........................... 204/182.8, 299 R, 204/301, 182.1; 424/484

[56] References Cited

U.S. PATENT DOCUMENTS

| | | | |
|---|---|---|---|
| 4,889,606 | 12/1989 | Dyson et al. | 204/182.8 |
| 5,159,049 | 10/1992 | Allen | 524/56 |

*Primary Examiner*—Nathan M. Nutter
*Attorney, Agent, or Firm*—Pennie & Edmonds LLP

[57] ABSTRACT

One aspect of the invention is to provide methods for the storage of electrophoresis gels, particularly, electrophoresis gels adapted for polynucleotide sequencing. The invention provides numerous methods of preparing a packaged electrophoresis gel or gel assembly. The subject methods include the steps of inserting an electrophoresis gel or gel assembly into the interior chamber of a storage container, removing air from the interior chamber, and hermetically sealing the storage container so as to provide a sealed package containing an electrophoresis gel in a reduced atmospheric environment. Preferably, the interior chamber is flushed with an inert gas prior to the sealing process. Another aspect of the invention is to provide packaged electrophoresis gels. The packaged electrophoresis gels include a hermetically sealed storage container having an interior chamber. The interior chamber contains a gel or gel assembly suitable for electrophoresis. The interior chamber of the storage container encloses a reduced atmospheric environment. Additionally, the interior chamber preferably contains a buffer solution. The storage container may comprise two sheets of flexible polymer which are fused to one another at or near the perimeter so as to form an interior chamber.

16 Claims, 1 Drawing Sheet

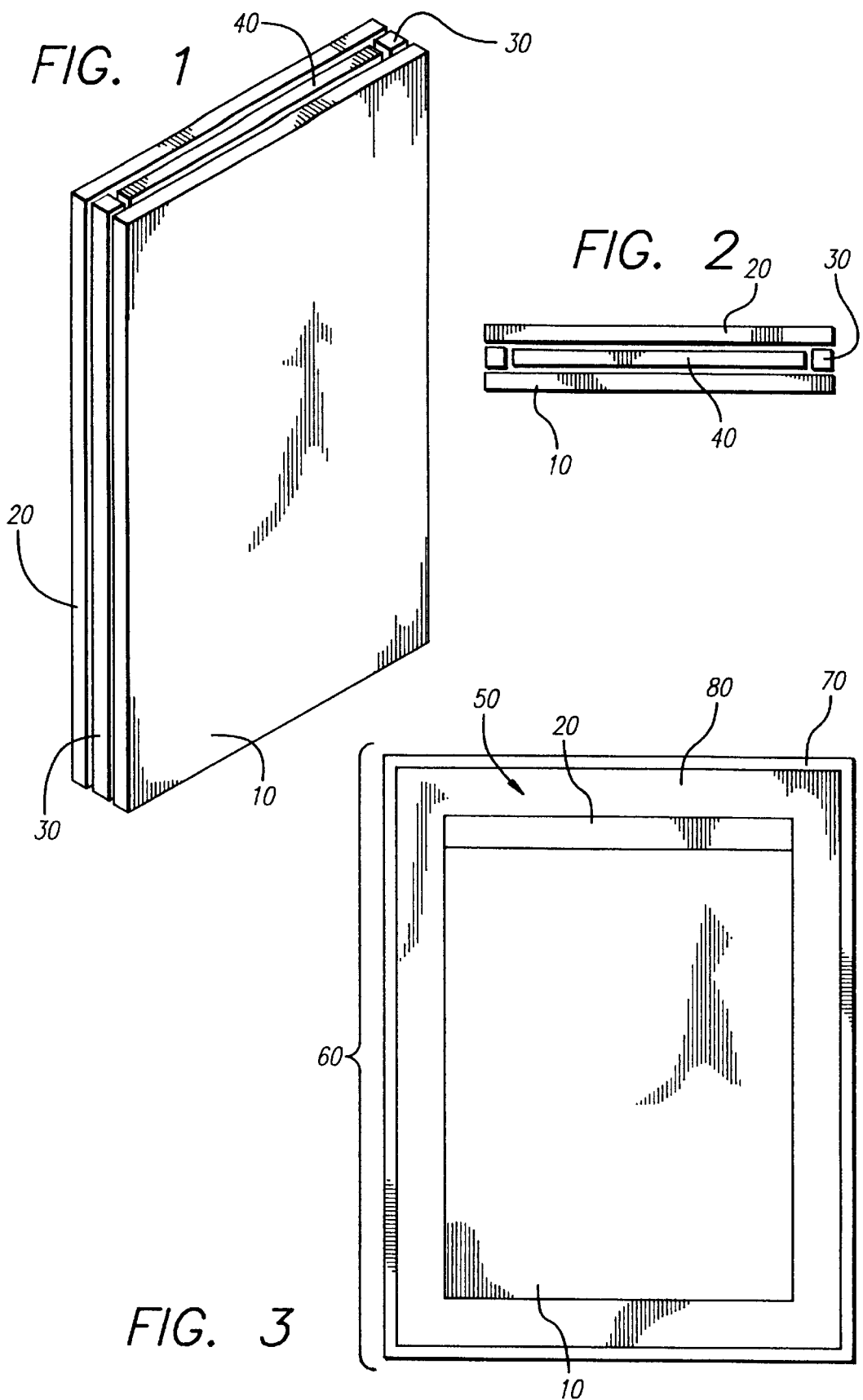

METHODS FOR STORAGE OF SEQUENCING GELS AND STORED SEQUENCING GELS USED BY SUCH METHODS

FIELD OF THE INVENTION

This invention is in the field of gel electrophoresis, and more specifically in the field of the storage of electrophoresis gels.

BACKGROUND

The technique gel electrophoresis is frequently used for the separation of proteins and nucleic acids. Gel electrophoresis is used in the sequencing of nucleic acids by both chain termination sequencing and Maxam and Gilbert sequencing. A major inconvenience in performing gel electrophoresis is the need to cast a gel. The casting of electrophoresis gels, particularly the casting of polyacrylamide gels, is time-consuming, involves manipulation of toxic chemicals, and frequently fails to produce the desired result. Moreover, the extremely large gels used for nucleic acid sequencing are particularly difficult and time-consuming to prepare. It is thus of interest to provide packaged pre-cast gels, especially nucleic acid sequencing gels, so as to expedite research and save valuable time. Although the use of pre-cast gels has been proposed in the past, numerous practical problems have arisen when storing electrophoresis gels, especially nucleic acid sequencing gels. Gels stored for prolonged periods of time, even 2–3 days, produce poor results when used for nucleic acid sequencing and other procedures. Packaged gels with a short storage life are of negligible practical use. Thus, there exists a need for methods of storing gels for use in electrophoresis for extended periods of time, as well as packaged electrophoresis gels produced by such methods.

SUMMARY OF THE INVENTION

One aspect of the present invention is to provide methods for the storage of electrophoresis gels, particularly, electrophoresis gels adapted for polynucleotide sequencing. Stored electrophoresis gels serve to increase the speed and accuracy with which the results of experiments may be obtained. The invention provides numerous methods of preparing a packaged electrophoresis gel or gel assembly. The subject methods comprise the steps of inserting an electrophoresis gel or gel assembly into the interior chamber of a storage container, removing air from the interior chamber, and hermetically sealing the storage container so as to provide a hermetically sealed package containing an electrophoresis gel. Preferably, the interior chamber is flushed with an inert gas prior to the vacuuming and sealing processes so as to facilitate the creation of a reduced atmospheric environment in the interior chamber of the storage container. In a preferred embodiment of the invention, the packaged gel (or gel assembly) is stored between 4° and 10° C.

Another aspect of the invention is to provide packaged electrophoresis gels or gel assemblies. The packaged gels of the invention may be stored for prolonged periods of time so as to provide electrophoresis gels when required. The subject gel and gel assembly packages comprise a hermetically sealed storage container having an interior chamber. The interior chamber comprises a gel or gel assembly suitable for electrophoresis. Suitable gels include polyacrylamide gels adapted for polynucleotide sequencing. The interior chamber of the storage container may be characterized as having a reduced atmospheric environment and preferably contains an inert gas. Additionally, the interior chamber preferably contains a buffer solution. In a preferred embodiment of the invention, the storage container comprises two flexible polymer sheets which are joined to one another at or near the perimeter so as to form an interior chamber.

BRIEF DESCRIPTION OF THE DRAWINGS

The invention may be better understood by reference to the specific embodiments shown in the following drawings.

FIG. 1. FIG. 1 shows a electrophoresis gel assembly. The first support plate is 10. The second support plate is 20. The spacers are 30. The electrophoresis gel is 40.

FIG. 2. FIG. 2 is an end view of the electrophoresis gel assembly of FIG. 1.

FIG. 3. FIG. 3 shows a packaged electrophoresis gel assembly in a container formed by two flexible polymer sheets. 10 is the first support plate of the gel assembly. 20 is the second support plate of the gel assembly. 50 is the interior chamber. 60 is the storage container. 70 are the seams of the storage container. 80 is a flexible polymer sheet that forms part of the storage container.

DESCRIPTION OF THE SPECIFIC EMBODIMENTS

The invention provides methods for the prolonged storage of electrophoresis gels. Gels, including DNA sequencing gels, stored by the methods of the invention may be used 90 days or more after casting. The storage methods involve placing one or more electrophoresis gels or gel assemblies in a hermetically sealed container having an interior chamber that encloses a reduced atmospheric environment. The invention also provides for packaged electrophoresis gels suitable for use in electrophoresis after prolonged storage. Polyacrylamide sequencing gels stored in accordance with methods of the invention may be stored for prolonged periods of time, including six months or more, and still be effective for use in polynucleotide sequencing. Gel electrophoresis is a well established technique in molecular biology and is frequently used to separate mixtures of various molecules including proteins and nucleic acids. Descriptions of how to make and use electrophoresis gels can be found in, among other places, Rickwood and Hames, *Gel electrophoresis of Nucleic Acid: A Practical Approach, Second Edition* IRL Press (1990), Griffin and Griffin, *DNA Sequencing Protocols: Methods in Molecular Biology Vol.* 23, Humana Press (1993), Sambrook et al., *Molecular Cloning A Laboratory Manual 2nd Ed.,* Cold Spring Harbor Press (1989). The term "electrophoresis gel," as used herein, refers to a variety of gels that may be used in the technique of gel electrophoresis and includes gels formed by a variety of gel matrix materials, including polyacrylamide, agarose, polyacrylamide-agarose composites, and the like. The term "gel assembly" as used herein refers to a unit comprising at least a gel and a support plate. Support plates 10 are generally rigid and may be made from a variety of materials including glass and plastic. Gel assemblies may further comprise a second support plate 20. Gel assemblies comprising a second support plate also comprise two spacers 30 (or equivalent means for maintaining a gap between support plates, thereby providing spacer for the gel). Spacers may be of uniform thickness or may vary continuously in thickness as a function of length. Gel assemblies may further comprise a well forming comb, e.g., a "sharks tooth comb". The gel may be covalently attached to a support plate. Gel assemblies are well known to the person of ordinary skill in the art Electrophoresis gels may be covalently attached to support plates by a variety of methods well known to the person of ordinary skill in the art. For example, the use of γ-methacryloxyproply-trimethoxy silane for covalent attachment of gels to plates is described in Garoff and Ansorge, Anal. Biochem. 115:450–457 (1981). Additionally, in gel assemblies comprising two support plates, one of the two support plates may be coated with a chemical, e.g., silane (as described in Garoff and Ansorge, supra), so as to facilitate the separation of the gel from the support plate.

The subject methods of storing an electrophoresis gel involve the production of a package comprising a hermetically sealed container having an interior chamber 50 containing either an electrophoresis gel or gel assembly. The interior chamber 50 of the gel packages produced by the subject methods contain, i.e., enclose, a reduced atmospheric environment. Preferably, the enclosed reduced atmospheric environment comprises residual inert gas. While the subject methods of storing an electrophoresis gel may be carried out anytime after the gel has solidified, the subject methods of gel storage are preferably carried out immediately after the gel has solidified, i.e., the time between gel solidification and gel storage should be as short as possible. Generally, the time between gel solidification and gel storage will be less than twelve hours, more preferably less than six hours, and still more preferably less than one hour. The subject methods comprise the step of (1) inserting one or more electrophoresis gels or gel assemblies into the interior chamber of a storage container, (2) removing air from the interior chamber so that the interior chamber contains, i.e., encloses, a reduced atmospheric environment, and (3) hermetically sealing the storage container. The term "reduced atmospheric environment" as used herein indicates about 10% of pressure (at sea level) or less, preferably lower than 5% of atmospheric pressure, more preferably less than 1% of atmospheric pressure.

The generation of a reduced atmospheric environment in the interior chamber, i.e., the vacuuming step, may be accomplished by a variety of means. Air may be removed physically or by chemical means. In a preferred embodiment of the invention, the interior chamber is flushed with an inert gas, such as nitrogen, helium, argon, krypton, and the like, and subsequently subjected to a vacuuming step to produce a reduced atmospheric environment. After the vacuuming step, the reduced atmospheric environment enclosed by the interior chamber may be at a pressure less than 10% of atmospheric pressure (at sea level), preferably less than 5% of atmospheric pressure, and more preferably less than 1% of atmospheric pressure. The precise amount of air removed in a given embodiment of the invention may vary; however, in a particularly preferred embodiment of the invention, substantially all air is removed. While the inventors believe that oxygen has an adverse effect on long term storage of electrophoresis gels, the invention may be practiced as described herein, irrespective of this theory, by decreasing the amount of air in the interior chamber. The term "inert gas" as used herein refers to a gas that does not significantly chemically interact with the electrophoresis gel and gel buffers used in the packaged gel. The precise means for effecting the step of hermetically sealing the storage container will vary with the design of the storage container. For example, when the storage container consists of two flexible polymer sheets 50, the sealing step involves the formation of a seam formed by applying heat to the polymer sheets so as to form a seam by fusing the sheets. Alternatively, the sealing step may be effected through other sealing means such as adhesives or my a mechanical sealing devices. The subject methods may be carried out by commercially available means. In a preferred embodiment of the invention, the gel storage method is performed with a vacuum sealer with a gas flush and liquid filling systems. One example of such a device is the GVS Vacuum Sealing Machine produced by Gramatech (Sun Valley, Calif.). The subject method may be performed by inserting a gel assembly into a bag (the bag being flat, rectangular and initially sealed on three edges) composed of a flexible polymer, e.g., nylon foil, and heat sealing the unsealed edge of the bag after a inert gas flush step. In a preferred embodiment of the invention, the subject method further comprises storing the packaged gel at a reduced temperature. The reduced temperature is below room temperature, and is preferably below 15° C.; however, the reduced temperature must be high enough to prevent freezing of the gel.

Preferred gels for use in the subject invention are polyacrylamide gels. Polyacrylamide gels for use in the invention may have a variety of concentrations, including the range of 2%–25%, preferably in the range of 3%–15%, and more preferably in the range of 2%–10%. Polyacrylamide gels for use in the invention may also have a variety of crosslinking concentrations. The electrophoresis gels for use in the subject invention preferably comprise various buffering compounds in the fluid phase of the gel. A preferred buffer for use in the methods and packaged gels of the invention is tris-borate buffer (abbreviated TBE, consisting essentially of 89 mM Tris borate, 2 mM EDTA, pH 8.9). Electrophoresis gels for use in polynucleotide sequencing procedures may be employed in the methods and packaged gels of the invention. Sequencing gels are polyacrylamide gels and contain a polynucleotide denaturant, typically 7M urea. Sequencing gels may be of a uniform gel concentration or the gel matrix may form a concentration gradient. The prolonged storage of sequencing gels is particularly surprising given that sequencing gels stored by conventional techniques must be used within 2 days after casting so as to avoid the formation of significant gel defects. Gels are generally rectangular in shape and may vary in size in accordance with the size of selected electrophoresis apparatus. The gels may also contain wells for sample loading.

Another aspect of the invention is to provide packaged electrophoresis gels and gel assemblies suitable for prolonged storage (FIG. 3). Packaged gels and gel assemblies that are capable of being used after prolonged storage also may be produced by the methods of the invention. The packaged electrophoresis gels and gel assemblies of the invention comprise a hermetically sealed container having an interior chamber 50, wherein the interior chamber encloses a reduced atmospheric environment, and a gel or gel assembly 10, 20, 30 and 40. The volume of the interior chamber is preferably, although not necessarily, twice the volume of the enclosed gel or gel assembly, and more preferably less than twice the volume of the enclosed gel or assembly. Ideally, the volume of the interior chamber is as small as possible so as to maintain contact between the storage buffer in the interior chamber and the gel. The gel or gel assembly is located within the interior chamber. In a preferred embodiment of the subject packaged gels, gel assemblies rather than gels are stored in the interior chamber. Gel assemblies comprising two support plates, wherein the gel is covalently attached to one of the support plates are particularly preferred for use in the subject invention. Gel assemblies, particularly gel assemblies comprising two plates, are easier to handle and are more damage resistant than single plate gel assemblies or gels that are not stored within an assembly. The interior chamber encloses a reduced atmospheric environment of less than 10% of atmospheric pressure (at sea level), preferably less than 5% of atmospheric pressure, and more preferably less than 1% of atmospheric pressure. In a most preferred embodiment of the invention, the reduced atmospheric environment enclosed by the interior chamber is substantially devoid of air. In a preferred embodiment of the invention, the interior chamber comprises residual inert gas such as nitrogen, helium, neon, argon, krypton and the like. The inert gas in the interior chamber may be introduced by an inert gas flushing step that precedes the vacuuming step, thus producing a reduced atmospheric environment that contains the inert gas in a concentration that is higher than in air. The interior chamber preferably comprises a storage buffer. Preferably, the storage buffer is essentially identical to the buffer in the liquid phase of the gel. The storage buffer serves to prevent desiccation of the gel during storage. The storage buffer is present in a quantity sufficient to contact all of the exposed surface of the gel, otherwise portions of the gel may become dehydrated, thus compromising sequencing results obtained from the gel. In a preferred embodiment of the invention, an inert gas is bubbled through the storage buffer prior to the introduction of the buffer into the interior chamber. Preferably, the bubbling of the inert gas through the storage buffer proceeds until the dissolved oxygen content of the buffer is less than 5% (as measured at 20° C.).

The storage container may be any of a variety of forms and materials, provided that the container comprises a hermetically sealed interior chamber of sufficient size to enclose a gel or gel assembly of interest. The storage container should be made of gas impermeable materials so as to provide for a hermetic seal. Preferably, the storage container is opaque to light. In a preferred embodiment of the invention, the storage container is formed by two flexible polymer sheets 80. The sheets are fused, i.e., joined, together at or near the perimeters so as to form an interior chamber. An example of suitable flexible polymeric materials is nylon foil. In other embodiments of the invention, the storage container may be rigid or semi-rigid. The storage container is made of a material that maintains structural integrity during storage at reduced temperatures. By generating a reduced atmospheric environment in the internal chamber of storage containers formed from flexible polymeric sheets, the volume of the internal chamber is minimized. The volume is minimized because external atmospheric pressure will serve to press the storage container sheets into close contact with the gel or gel assembly in the storage container.

Other embodiments of storage containers include boxes with removable lids. Storage containers may comprise one or more valve regulated ports for controlling the flow of liquids and gases into and out of the interior chamber. The valve regulated ports may be used to facilitate one or more steps of the subject methods, e.g., the vacuuming of the interior chamber, the addition of storage buffers to the interior chamber, and the like.

Other embodiments of the invention include packaged electrophoresis gels and gel assemblies that have been produced by the methods of the invention. Such packaged electrophoresis gels (or gel assemblies) may be made by inserting an electrophoresis gel (or gel assembly) into the interior chamber of a storage container, vacuuming the interior chamber so as to produce a reduced atmospheric environment, and hermetically sealing the storage container. Preferably, a storage buffer is added to the storage container prior to the vacuuming step. In a preferred embodiment of the invention, the interior chamber is flushed with an inert gas prior to vacuuming.

Packaged electrophoresis gels and gel assemblies of the invention are preferably stored below 20° C. prior to use, more preferably below 15° C., and in a particularly preferred embodiment of the invention, at temperatures within the range of 4° C.–10° C. The packaged gels and gel assemblies should not be exposed to freezing temperatures for prolonged periods of time. While storage at reduced temperatures increases shelf life of the packaged gels produced by the methods of the invention, the packaged gels may be subjected to higher temperatures, e.g., room temperature (25° C.–30° C.) for several days so as to provide for the convenient shipping and handling of the packaged gels and gel assemblies.

The following examples are offered by way of illustration of the invention, and should not be interpreted as a limitation of the invention.

EXAMPLES

Sequencing gels were prepared according to the following procedure.

1. 24% Acrylamide 19:1 with 7m urea and 1×TBE (TBE is tris-borate EDTA buffer:89 mM Tris-borate, 2 mM EDTA, 8.9):

228 grams acrylamide 12 grams bis-acrylamide 420 grams urea 800 ml deionized $H_2O$ Urea, bis-acrylamide, and acrylamide were added to deionized $H_2O$. The solution was stirred using a stirring hot plate until dissolved. A small amount of heat may be needed to bring acrylamide and bis-acrylamide into solution.

10 grams of AG 501-X8 (D) deionizing resin was added and stirred for about 30 min.

The resin was removed by vacuum filtering through a 2 micron filter.

100 ml of 10×TBE buffer was added to the filtered solution and stirred until mixed thoroughly.

Deionized $H_2O$ was added to bring the volume to 1 liter, followed by more stirring.

The solution was stored at 4° C. in a foil wrapped bottle.

2. 7m urea and 1×TBE buffer solution 420 gr urea 800 ml deionized $H_2O$

Stir until dissolved, add 10 gr deionized resin, stir for 15 min.

Remove resin by vacuum filtering through a 2 micron filter

Add 100 ml 10×TBE buffer, stir well.

Add deionized $H_2O$ to bring the volume up to 1 liter, stir

Store at 4° C. in a foil wrapped bottle 3. 6% acrylamide solution (recipe makes 400 ml)

100 ml 24% bis:acrylamide 7m urea 1×TBE 300 ml 7m urea 1×TBE buffer solution swirl in flask to mix. The solution should not be agitated, as air will be introduced, inhibiting polymerization.

4. 25% ammonium persulfate solution 2.5 gr ammonium persulfate 10 ml deionized $H_2O$ The solution was mixed thoroughly by vortexing until all of the persulfate was dissolved.

Sequencing gels were poured between two 3 mm thick glass plates (support plates) separated by 0.25 mm spacers, and became covalently bound to the shorter glass plate. This binding was accomplished by coating the plate with approximately 300 μl of 3:1 (v/v) 10% acetic acid: 0.5% gamma-methacryloxypropyltrimethoxysilane in ethanol. The plate was then allowed to dry. The short and long plates were then assembled in a casting chamber that allows multiple plates to be held tightly together. This casting chamber used was a sealed unit with a port at the bottom for introduction of the acrylamide solution. A 24% solution of 19:1 bis-acrylamide/acrylamide was reduced to 6% by the addition of three parts 1XTBE/7m Urea buffer to one part acrylamide. Both the acrylamide and buffer solutions had been previously placed under a room temp vacuum of 150 mm HG, without stirring, for 20 minutes. 350 ml of the 6% acrylamide solution was poured into a beaker, 500 μl of 25% ammonium persulfate solution and 250 μl of TEMED were then added, stirred, and pumped into the casting chamber containing 10 sets of gel plates. Once the solution reached the top of the long plate, the pumping was stopped, and the connection was plugged in order to keep the casting chamber full. Spacers with a thickness of 0.25 mm and a width of 16 cm were then placed approximately 6 mm deep into the top of the gel sandwiches to create a gel to comb interface. This interface was to place the comb into the gel, thereby creating wells in which to place samples. Upon polymerization, the casting cassette was disassembled and the gels removed. The gels were then rinsed under deionized water, and the top spacer removed. Nylon foil poly bags 7¾"×19" Mil B-131-C1 from Shannon Packaging Co. of Covina, Calif. were used as storage containers. The gels were placed into these bags, and approximately 20 ml of 1XTBE/7M urea was added. The bag was then flushed with nitrogen gas for 3 seconds, vacuumed for 4 seconds to remove all air and gas, then heat sealed. This process was carried out with a GVS Vacuum Sealing Machine produced by Gramatech (Sun Valley, Calif.). The open end of the film foil poly bag was placed over a nozzle of a flush/vacuum/seal machine. This machine sealed the bag around the nozzle, and introduced an inert gas, such as nitrogen, into the bag. The machine then pulled a vacuum through the same nozzle, thus depleting the majority of the gas, along with any dilute air from the bag. The machine then heat sealed the bag while under vacuum, producing a package that is virtually devoid of air, i.e., a reduced atmospheric environment. The gels were then stored in a 4° C. refrigerator. The film foil bags are light tight, and do not breathe. A vertical gel device was used for the running of the gels. The samples were loaded into wells created by a shark's tooth comb that was inserted by the end user. Once the gels were packaged, they were placed into a 4° C. refrigerator.

Results

Gels in storage at 4° C. for over 7 months showed no appreciable deterioration in band resolution when used to resolve DNA sequencing reactions. These gels were run on a vertical gel device using Sequenase™ 2.0 and single-stranded M13 DNA. The bands on these gels are of high quality resolution. Additional experiments were performed to find the parameters necessary for storing the gels. These experiments have shown that air has the greatest effect on storage. Gels stored with a nitrogen flush prior to vacuuming had better band resolution after three months than those vacuumed only, and the poorest resolution was seen on those gels that were packaged and stored with air present. It appears that the nitrogen flush (or flush with a similar inert gas) is required for stable storage in excess of 60 days.

Experiments were performed to compare storage duration of sequencing gels under a variety of conditions. Experiments were performed in which sequencing gels were packaged without the removal of air; these gels became unusable after approximately 60 days. Experiments were also performed to measure the shelf life of the gels that were vacuumed only, and not flushed with an inert gas; these gels had a shelf life of between 3 and 4 months. The gels that were packaged with the gas flush, vacuum and then seal method and stored in a 4° C. refrigerator, have shown they were still usable after 1 year in storage. Gels that were packaged with the gas flush, vacuum, seal method were also stored at room temperature, to find the optimal storage method. Gels stored at room temperature were virtually unusable after 30 days storage.

Equivalents

The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

What is claimed is:

1. A packaged electrophoresis gel comprising a hermetically sealed storage container having an interior chamber, an electrophoresis gel, a storage buffer, wherein the gel and buffer are located within said interior chamber, and wherein the interior chamber encloses a reduced atmospheric environment.

2. A packaged electrophoresis gel according to claim 1, wherein the electrophoresis gel is a polyacrylamide gel.

3. A packaged electrophoresis gel according to claim 2, wherein the gel comprises urea.

4. A packaged electrophoresis gel according to claim 2, wherein the buffer is a tris borate buffer.

5. A packaged electrophoresis gel according to claim 1, wherein the storage container comprises two sheets of a flexible polymer.

6. A packaged electrophoresis gel according to claim 5, wherein the flexible polymer is nylon foil.

7. A packaged electrophoresis gel according to claim 1, wherein the electrophoresis gel is part of a gel assembly, said gel assembly comprising a support plate.

8. A packaged electrophoresis gel according to claim 2, wherein the electrophoresis gel is covalently attached to the support plate.

9. A packaged electrophoresis gel according to claim 1, wherein the interior chamber comprises an inert gas.

10. A method of preparing a packaged electrophoresis gel, said method comprising the steps, inserting an electrophoresis gel into the interior chamber of a storage container, vacuuming said interior chamber, whereby a reduced atmospheric environment is produced, and hermetically sealing said storage container.

11. A method of preparing a packaged electrophoresis gel according to claim 10, wherein the vacuuming step comprises the step of flushing the interior chamber with an inert gas.

12. A method of preparing a packaged electrophoresis gel according to claim 10, wherein the electrophoresis gel is a polyacrylamide gel.

13. A method of preparing a packaged electrophoresis gel according to claim 12, wherein the electrophoresis gel comprises urea.

14. A packaged electrophoresis gel produced by a method according to claim 10.

15. A packaged electrophoresis gel produced by a method according to claim 11.

16. A packaged electrophoresis gel produced by a method according to claim 12.

* * * * *